United States Patent [19]

Kosugi et al.

[11] 4,013,512
[45] Mar. 22, 1977

[54] METHOD FOR ADSORPTION AND ELUTION OF LIPID HYDROLYZING ENZYMES

[75] Inventors: Yoshitsugu Kosugi; Hideo Suzuki; Akira Kamibayashi, all of Chiba, Japan

[73] Assignee: Agency of Industrial Science & Technology, Tokyo, Japan

[22] Filed: Sept. 18, 1974

[21] Appl. No.: 507,050

[30] Foreign Application Priority Data

Nov. 19, 1973 Japan ............................ 48-129919

[52] U.S. Cl. ............................... 195/66 R; 195/63
[51] Int. Cl.² .......................................... C07G 7/02
[58] Field of Search ........................... 195/66 R, 63

[56] References Cited
UNITED STATES PATENTS 3,649,455  3/1972  Abe et al. ...................... 195/66 R

OTHER PUBLICATIONS

Er-el et al., "Hydrocarbon-Coated Sepharoses. Use in the Purification of Glycogen Phosphorylase," Biochemical & Biophysical Research Communications 49:2 (1972), pp. 383-390.

Hofstee, "Protein Binding by Agarose Carrying Hydrophobic Groups," Biochemical & Biophysical Research Communications 50:3 (1973), pp. 751-757.

Advances in Enzymology, vol. 36, pp. 29-89, pp. 29 and 46-50, 1972.

*Primary Examiner*—A. Louis Monacell
*Assistant Examiner*—C. A. Fan
*Attorney, Agent, or Firm*—Oblon, Fisher, Spivak, McClelland & Maier

[57] ABSTRACT

A lipid hydrolyzing enzyme-containing substance is brought into contact with an insoluble carrier having a hydrophobic organic compound attached thereto in the form of a hydrophobic residue so that the lipid hydrolyzing enzyme is adsorbed by the hydrophobic residue attached to the insoluble carrier. Then, the lipid hydrolyzing enzyme adsorbed on the carrier is isolated by elution.

11 Claims, 3 Drawing Figures

METHOD FOR ADSORPTION AND ELUTION OF LIPID HYDROLYZING ENZYMES

BACKGROUND OF THE INVENTION

This invention relates to a method for separating a lipid hydrolyzing enzyme from a substance or crude solution containing the lipid hydrolyzing enzyme by bringing the said lipid hydrolyzing enzyme-containing substance or crude lipid hydrolyzing enzyme solution into contact with an insoluble carrier having a hydrophobic organic compound attached thereto in the form of a hydrophobic residue and thereby causing the lipid hydrolyzing enzyme to be adsorbed on the insoluble carrier having attached thereto the hydrophobic residue. It also relates to a method for obtaining the lipid hydrolyzing enzyme in high purity by eluting the said lipid hydrolyzing enzyme from the carrier on which it has been adsorbed by the aforementioned method.

As enzymes capable of hydrolyzing fats, lipid hydrolyzing enzymes are known to occur widely in the biological world and are utilized as digesters. In addition, they are being applied in newly developed fields such as in flavor enzymes, leather tannery, oils' and fats' decomposition, detergents, cosmetic goods, animal feeds, brewing and fermentation. Researches are now under way aimed at utilization of the specificity of lipid hydrolyzing enzymes for the determination of chemical structures of glycerides. There is every indication that lipid hydrolyzing enzymes will become usable in the future for the preparation and interesterification of monoglycerides, diglycerides, triglycerides, esters, etc.

If lipid hydrolyzing enzymes are present in preserved foodstuffs and medicines and drugs, they cause oils and fats contained in these products to be enzymatically decomposed. Thus, necessity is felt for development of a technique capable of removing the lipid hydrolyzing enzymes from the products.

There exist various kinds of lipid hydrolyzing enzymes which have proteinaceous properties differing slightly from one another depending on particular species and structures of the organisms by which they are produced. Moreover there also occur various kinds of biological high molecular compounds having affinity for hydrophobic residues, such as lipids, lipoproteins and enzymes connected to lipoidic metabolism. In order for specific lipid hydrolyzing enzymes to be isolated and refined from among these various biological high molecular compounds, it becomes necessary to effect the operations of adsorption and elution by respective different methods which are proper to the particular kinds of lipid hydrolyzing enzymes.

For the promotion of the advantageous utilization and control of such lipid hydrolyzing enzymes functions, it is found necessary to develop a method which permits economic and easy isolation and refinement of lipid hydrolyzing enzymes and a method which provides specific removal of lipid hydrolyzing enzymes. The conventional method for purification is only a combination of ordinary methods adopted for the refinement of enzymes in general. Only a few methods cited herein below are known to make effective use of the characteristics of lipid hydrolyzing enzymes. For the removal of lipid hydrolyzing enzymes, the only method available is by inactivating lipid hydrolyzing enzymes under heat. Microorganisms of genus *Pseudomonas* produce highly heat-resistant lipid hydrolyzing enzymes. For the purpose of removal, therefore, these lipid hydrolyzing enzymes must be heated at a high temperature for a long time. In this case, the heating has an adverse effect.

As concerns adsorption and isolation of lipid hydrolyzing enzymes by effective use of their characteristics, Willstatter et al. reported long ago that stearic acid powder adsorbed lipid hydrolyzing enzymes (R. Willstatter, E. Waldschmidt - Leitz, Fr. Memmen: Z. Physicl. Chem., 125, 93 (1923)), Sarda et al. reported their observation that lipid hydrolyzing enzymes adsorbed on the emulsion of a long-chain triglyceride migrated into the water phase when the emulsion was destroyed by addition of diethyloxide (L. Sarda, G. Marchis - Mouren, P. Dosnuelle: Biochim. Biophys. Acta., 24, 425 (1957)) and Fielding made an observation that lipoprotein lipase bound itself with a substrate and consequently formed a complex and succeeded in refining enzymes by utilizing the specificity of lipoprotein lipase. To be more specific, a substrate-enzyme complex was obtained by adding lipid emulsion to a plasma containing lipoprotein lipase and subsequently separating the precipitate by means of centrifugation. He washed this complex thoroughly, treated the washed complex with 0.3% sodium deoxychlate to remove a lipid hydrolyzing enzyme from fats and subjected it to subsequent refinement (C. J. Fielding: Biochim. Biophys. Acta., 178, 499 (1969)).

These methods, however, entail various disadvantages. For example, separation of lipid hydrolyzing enzymes and adsorbents is difficult to accomplish, lipid hydrolyzing enzymes decompose adsorbents to consequently render subsequent refining operations difficult, the operations of adsorption and isolation are carried out batchwise and therefore do not permit continuous adsorption by the column-packing technique or adoption of column chromatography, and so on. These methods are imperfect as techniques to be adopted for specifically removing, isolating and refining lipid hydrolyzing enzymes. Thus, they have hardly departed from the domain of laboratory expedients.

An object of this invention is to provide a commercially practicable method for removing a lipid hydrolyzing enzymes from a substance containing the lipid hydrolyzing enzymes.

Another object of this invention is to provide a commercially feasible method for isolating and refining a lipid hydrolyzing enzyme.

Still another object of this invention is to provide a method capable of continuously removing a lipid hydrolyzing enzyme from a crude lipid hydrolyzing enzyme-containing solution and refining the removed lipid hydrolyzing enzyme.

SUMMARY OF THE INVENTION

To attain the objects described above, the method according to the present invention causes a lipid hydrolyzing enzyme-containing substance or a crude lipid hydrolyzing enzymes solution to be brought into contact with an insoluble carrier having a hydrophobic organic compound attached thereto in the form of a hydrophobic residue and thereby causing the lipid hydrolyzing enzyme to be adsorbed by the hydrophobic residue. This invention subsequently accomplishes the isolation and refinement of the adsorbed lipid hydrolyzing enzyme by causing the lipid hydrolyzing enzyme adsorbed on the hydrophobic residue attached to the insoluble carrier to be eluted with a surface active agent, a protein denaturing agent or an organic solvent miscible with water. From the eluted lipid hydrolyzing enzyme can be easily obtained by a known method.

Other characteristics and other advantages of this invention will become apparent from the description to be given in further detail herein below with reference to the accompanying drawings.

DETAILED DESCRIPTION OF THE INVENTION

In the present invention, lipid hydrolyzing enzymes are adsorbed by the hydrophobic residue of an adsorbent, namely a hydrophobic organic compound, attached to an insoluble carrier.

The insoluble carriers usable for the present invention include agarose, dextran, polyacrylamide, cellulose, polystyrene, nylon and glass which are used as insoluble carriers for affinity chromatography. That is to say, any insoluble carrier may be used insofar as the carrier has a coarse structure such as to permit ready approach between the lipid hydrolyzing enzyme and the adsorbent. Particularly agarose is a desirable insoluble carrier becuase it is hydrophilic and practically inert chemically and it has no possibility of causing unnecessary interaction with proteins.

In the present invention, it is the hydrophobic residue of the hydrophobic organic compound that provides specific adsorption of the lipid hydrolyzing enzyme. The term "hydrophobic organic compound" as used herein refers generally to an organic compound of the type having more hydrophobic residues than hydrophilic residues. From this, it follows that as an adsorbent, i.e. a substance serving the purpose of effecting the aforementioned adsorption of the lipid hydrolyzing enzyme, there may be used any hydrophobic organic substance insofar as it satisfies the aforementioned definition. In the case of an aliphatic adsorbent, any of the aliphatic compounds having seven or more carbon atoms is used advantageously. Compounds including fats of even-numbered carbon atoms have been demonstrated to exhibit particularly desirable results. When an aliphatic compound having fewer carbon atoms is attached to an insoluble carrier, the distance between the carrier and the hydrophobic residue is so small that the expected interaction between the hydrophobic residue and the lipid hydrolyzing enzyme fails to proceed smoothly. These aliphatic compounds having fewer carbon atoms can be improved in affinity by incorporating a suitable spacer which is otherwise known as an arm. (Refer to E. Steers et al.: J. Biol. Chem., 246, 196 (1971)) Aliphatic compounds having even-numbered carbon atoms do not occur abundantly in nature. The fact that lipid hydrolyzing enzymes have an affinity for these aliphatic compounds suggests that the affinities of the lipid hydrolyzing enzymes show for aliphatic compounds are not highly specific.

Further, aromatic, alicyclic and heterocyclic hydrophobic compounds are also usable as adsorbents. For example, aromatic compounds such as benzene and chrysene, alicyclic compounds such as cyclohexane and deoxycholic acid and heterocyclic compounds such as pyridine are suitable for use. When an adsorbent is attached directly to an insoluble carrier, it sometimes happens that the distance between the carrier and the hydrophobic residue will become too small for the interaction of the adsorbent and the lipid hydrolyzing enzyme to proceed smoothly. In such a case, the stearic hindrance which would possibly occur on the insoluble carrier at the time of adsorption of the lipid hydrolyzing enzyme can be precluded by introducing a suitable spacer.

Various methods are available for the attachment of the hydrophobic organic compound to the insoluble carrier contemplated by this invention: A method whereby agarose or dextran is activated by use of cyanogen bromide and then allowed to react directly with a primary amine derivative as an adsorbent, a method whereby an amino-alkyl acid is attached to an insoluble carrier preparatorily activated with cyanogen bromide and the resultant insoluble carrier having the aminoalkyl acid attached thereto is coupled with a primary amine derivative, a method whereby a diamine compound is attached to an insoluble carrier activated in advance with cyanogen bromide and the diamine compound on the carrier is coupled with an adsorbent containing a carboxylic group, a method whereby an insoluble carrier of bromoacetyl is coupled with an adsorbent containing a primary amine and an imidazole compound (P. Cuatrecasas: J. Biol. Chem., 245, 3059 (1970)), a method whereby an adsorbent containing an amino group is coupled with a succinylamino propyl derivative (J. D. Berman, M. Young: Proc. Nat. Acad. Sci., 68, 395 (1971)) and a method whereby an adsorbent containing a carboxylic group is coupled with a thiol derivative (P. Cuatrecasas: J. Biol. Chem., 245, 3059 (1970)) are examples.

When the hydrophobic adsorbent is attached to the insoluble carrier, the desired attachment can be accomplished advantageously by having the adsorbent reacted upon in about 50% of an organic solvent such as, for example, dioxane, ethylene glycol, methanol, ethanol or acetone. If an anhydrous alcohol or some other similar solvent is used in this case, the dehydrating activity of this solvent may deprive the insoluble carrier of its coarse structure and consequently obstruct the required interaction between the adsorbent and the protein. For this reason, it is desirable that the solvent of this type be maintained below the lowest concentration at which the dehydration activity is exhibited. After the adsorbent has been attached to the insoluble carrier, the unaltered portion of the adsorbent is removed by washing the carrier alternately with an acid and an alkali each containing the aforementioned organic solvent and about 1M of a salt. If, in this case, there is an excess of active residue, this residue may as well be protected by use of about 1M of ethanolamine solution (pH 8.0) containing about $0.5\mu$ of common salt or a short-chain aliphatic amine solution prior to the aforementioned removal of the unaltered adsorbent.

Now, a description will be given of the method by which a substance containing a lipid hydrolyzing enzyme is brought into contact with the insoluble carrier having attached thereto the hydrophobic residue of a hydrophobic organic compound so as to have the lipid hydrolyzing enzyme adsorbed by the hydrophobic residue on the carrier.

In terms of practical operation, this method is carried out by either of the two processes, i.e. batchwise process and column process.

The batchwise process is one in which the insoluble carrier, in preparation for the attachment of the hydrophobic organic compound thereto, is dispersed and shaken for some time in a liquid containing a lipid hydrolyzing enzyme (such as, for example, a protein solution) and thereafter this insoluble carrier is separated as by filtration or centrifugation from the solution containing the dissolved lipid hydrolyzing enzyme. The column process is one in which the aforementioned insoluble carrier is packed in a column and a liquid containing a lipid hydrolyzing enzyme (such as, for example, a protein solution) is caused to run through the column under suitable conditions.

Neucleic acids, carbohydrates and other proteinaceous molecules which are contained in the aforementioned solution are adsorbed very little because, in the solution, they assume a three-dimensional configuration such that hydrophobic residues are enveloped deep inside and hydrophilic residues alone are exposed on the surface. A low-molecular surface active agent notably decreases the amount of a lipid hydrolyzing enzyme to be adsorbed. It is, therefore, desirable that the protein solution be deprived of such unwanted substance in advance by dialysis or filtration with a gel, for example. The amount of the insoluble carrier to be used must be increased in direct proportion to the volume of the protein solution subjected to treatment. On the other hand, the amount of a lipid hydrolyzing enzyme which is adsorbed per unit quantity of the insoluble carrier having attached thereto the hydrophobic residue similarly increases with the increasing lipid hydrolyzing enzyme concentration in the solution. Since the adsorption of the lipid hydrolyzing enzyme by the hydrophobic residue occurs in more cases in the form of hydrophobic bonding rather than in the form of an ionic bonding or physical adsorption, the adsorbed lipid hydrolyzing enzyme is not eluted by a highly concentrated salt solution or a buffer solution having a pH value in the range in which the enzyme does not undergo any irreversible conversion. When the insoluble carrier is washed with such salt solution or buffer solution, therefore, ordinary proteins, nucleic acids and carbohydrates can be removed because of their lack of affinity for the hydrophobic residue and the adsorbed lipid hydrolyzing enzyme can be improved in terms of purity.

In the present invention, the term "lipid hydrolyzing enzyme-containing substances" is so extensive as to embrace preserved foodstuffs, for example. By the application of the method described above, lipid hydrolyzing enzymes such as, for example, lipases which are present in foodstuffs can be removed.

An explanation will be given herein below of the method by which the lipid hydrolyzing enzyme adsorbed by the hydrophobic residue of the hydrophobic organic compound attached to the insoluble carrier is isolated and refined.

This method consists in eluting the adsorbed lipid hydrolyzing enzyme. This elution is effected by any of the methods described below: A method whereby the lipid hydrolyzing enzyme is eluted by causing the link formed between the protein of the lipid hydrolyzing enzyme and the hydrophobic residue to be distorted such as with a protein denaturing agent, a method whereby the elution is accomplished by use of a surface active agent and a method whereby the elution is caused by means of an organic solvent miscible with water are examples. First, the method resorting to the protein denaturing agent will be explained.

Examples of the protein denaturing agents usable for this method are guanidine hydrochloride and urea. For the purpose of practical operation, this protein denaturing agent is required to be used at a high concentration of about 5M.

Then, the method involving the use of the surface active agent will be explained.

The elution can be accomplished by use of such bile salts as sodium taurocholate, sodium glycocholate, sodium cholate and sodium deoxycholate which are surface active agents of organic origin. The concentration at which such salt is used is appropriate in the range of from 0.2 to 0.4%. The activity of lipid hydrolyzing enzymes is not reduced by bile salts. Some lipid hydrolyzing enzymes such as pancreas lipase are even activated by bile salts in the neighborhood of elution concentration. It is interesting to note that the concentration of bile salts suitable for the elution is in agreement with the concentration thereof within the small intestines of higher animals at the time of digestion. The relationship between the insoluble carrier and the lipid hydrolyzing enzyme in terms of the elution of the latter constitutes itself a model for lipid hydrolysis within the small intestines and, therefore, can serve as an important tool for the developmental researches relating to artificial internal organs and surface chemistry.

Further, the elution can also be accomplished by use of anionic surface active agents such as sodium oleate and sodium lauryl sulfate, nonionic surface active agents such as Tween 29 (Trademark for a proprietary product of polyethylene sorbitan monolaurate), Tween 80 (Trademark for a proprietary product of polyethylene sorbitan monoleate) and Triton X 100 (p-t-octylphenoxypolyethoxy ethanols) and amphoteric ionic surface active agents such as Lipomin COH (Trademark for a proprietary product of 1-hydroxyethyl-1-carboxylsodium 2-alkyl-2-imidazolinium hydroxide, manufactured by Lion Armour Co. Ltd.). These surface active agents are not derived from organic origins as are bile salts and, therefore, are inexpensive, permitting a large quantity of a lipid hydrolyzing enzyme to be refined economically in high yields. Some of the synthetic surface active agents impede the activities of lipid hydrolyzing enzymes. This adverse effect can be removed by subjecting such synthetic products to dialysis or dilution. Although the concentration at which the surface active agent is used varies with the particular kind of the agent, good results are obtained by using the surface active agent at a concentration higher than the critical micelle concentration at which the micellar formation of the surface active agent takes place.

The elution effected by the surface active agent may logically be explained by a postulate that the surface active agent dissolved in water is displaced for the lipid hydrolyzing enzyme which is adsorbed on the hydrophobic residue. Accordingly, the surface active agent is adsorbed on the insoluble carrier having attached thereto the hydrophobic residue and the adsorbed surface active agent is eluted by addition of the lipid hydrolyzing enzyme solution. This phenomenon can easily be observed by using a surface active agent labelled with a radioisotope. The inactivation of the lipid hydrolyzing enzyme by the surface active agent is observed when the said enzyme is left to stand for a long time in some kind of a surface active agent solution. For this reason, it is desirable that the eluate be deprived of the surface active agent by dialysis, filtration or some other suitable means.

It is also possible to effect the elution of the adsorbed lipid hydrolyzing enzyme by use of such organic solvents as ethanol, methanol, acetone, dioxane and ethylene glycol which are miscible with water. When an anhydrous alcohol or a similar solvent is used, the dehydrating activity of this solvent deprives the insoluble carrier of its coarse structure. For this reason, it is desirable that the concentration of anhydrous alcohol be maintained below the lowest level of about 50% at which the said dehydrating activity is exhibited. Although water suffices as the liquid for intimate blending with the organic solvent, a buffer solution having a suitable pH value and a proper salt concentration provides better recovery of activity.

This method accomplishes the elution of the lipid hydrolyzing enzyme by use of an organic solvent miscible with water. The elution conditions, therefore, can be varied to suit the circumstances by properly selecting the concentration of the organic solvent and the pH value and ionic strength of the buffer solution to be intimately mixed with the organic solvent. In this respect, this method proves advantageous for mutual fractionation of biological high molecular compounds having strong affinity for lipids. Moreover, solutions of these organic solvents seldom denature lipid hydrolyzing enzymes and are inexpensive, and they are easily removed by dialysis, filtration with gel or distillation and can be recovered for cyclic use. Unlike the surface active agents, they have no possibility of being adsorbed on the insoluble carrier having attached thereto the hydrophobic residue, permitting simple regeneration of the used insoluble carrier. Because of these advantages, this method promises well as a commercially feasible process for the isolation and refinement of lipid hydrolyzing enzymes.

In terms of actual procedure, this method of elution is accomplished by either of the following processes: They are a batchwise process whereby the insoluble carrier having adsorbed thereon the said enzyme is dispersed in a liquid containing a suitable eluting agent and the column process whereby the insoluble carrier having adsorbed thereon the said enzyme is packed in a column and the eluting agent is caused to run through the column.

The used insoluble carrier can easily be regenerated and put to cyclic use. To be specific, this is accomplished by first causing the uneluted lipid hydrolyzing enzyme remaining adsorbed on the insoluble carrier to be eluted by denaturing the enzyme by use of the aforementioned eluting agent or through a suitable physical or chemical treatment and thereafter washing the carrier alternately with an acid and an alkali. The insoluble carrier can be recycled so long as it is regenerated as described above.

The kinds of lipid hydrolyzing enzymes to which the present invention can be used range extensively from lipases of higher animals to lipases of yeasts and microorganisms. Because of the substratal specificity, the present invention is also applicable to those lipid hydrolyzing enzymes which are called lipoprotein lipases, esterases and phospholipases. To lipids, lipoproteins and proteins having strong affinity for the hydrophobic residues participating in the lipoidal metabolism, the present invention can also be applied by modifying the conditions to some extent.

The conventional method for the refining of biological high molecular compounds has been intended for spherical proteins enveloped in hydrophilic residues. In contrast, the method for refinement contemplated by the present invention is aimed at lipid hydrolyzing enzyme molecules and other hydrophobic residues which are exposed to the surface. The adsorbing activity, therefore, is specific to biological high molecular compounds having strong affinity for lipids. Effective utility of this specific adsorbing activity leads to establishment of a technique which is useful for the removal of lipid hydrolyzing enzyme contained in solutions, which technique permits production of a highly refined specimen. When lipid hydrolyzing enzymes having strong affinity for lipids and enzymes participating in lipoidal metabolism are refined to a high degree of purity, the resultant products will not only contribute to the advancement of researches on lipoidal metabolism but serve as important substances for clinical medicine relating to digestion and assimilation of nutrients and to blood circulation. They may possibly serve as important catalysts in the fine chemical industry for hydrolysis of oils and fats, interesterification, synthesis of esters, determination of chemical structures of triglycerides, etc.

The present invention will be described in further detail herein below with reference to preferred embodiments, which are not limitative of this invention in any way.

EXAMPLE 1

In 5ml of a 1:1 mixed solution consisting of ethanol and 0.1M sodium hydrogen carbonate containing therein 0.5M common salt having dissolved therein 10mg of a different adsorbent shown in Table 1, there was dispersed 3.4ml of Sepharose 4B activated in advance with cyanogen bromide. The resultant dispersion was shaken at normal room temperature for two hours to effect a reaction. The reaction mixture was passed through a glass filter and the filter cake was dispersed in 5ml of 1M ethanolamine solution containing 0.5M common salt (pH 8.0) and shaken at room temperature for two hours to cause a reaction, with the result that the preparation of a carrier was completed with the unimpaired active residue kept from the reaction.

Then, the prepared carrier was washed cyclically with a 1:1 mixed solution consisting of ethanol and 0.1M sodium hydrogen carbonate solution containing 0.5M common salt, 0.1M acetate buffer solution containing 1M common salt (pH 4.0) and a borate buffer solution containing 1M common salt (pH 8.0) in the order mentioned to remove substances which were bound to the carrier by virtue of physical adsorbing activity. The washed insoluble carrier was equilibrated with Tris (hydroxymethyl) aminomethane-HCl buffer (pH 8.0) having an ionic strength of 0.02 (hereinafter referred to as "Tris buffer") and put to use in the test described below. An inoculum of *Pseudomonas me-*

*phitica* var. *lipolytica* was aerobically incubated at 30° C for 24 hours in a medium incorporating 3% of defatted soy flour, 0.5% of $K_2HPO_4$, 0.03% of $MgSO_4 \cdot 7H_2O$ and 0.56% of oleic acid. At the end of the incubation, the incubated solution was centrifuged for ten minutes at 6000 × g. The resultant supernatant represented a lipid hydrolyzing enzyme solution produced extraceullarly by the microorganisms of genus *Pseudomonas*. This solution was adjusted to pH 4 to cause precipitation and the precipitate consequently formed was extracted by adjusting the solution to pH 8 to afford a crude lipid hydrolyzing enzyme solution.

The insoluble carrier prepared as described above was dispersed in 5ml (208 units) of the aforementioned crude lipid hydrolyzing enzyme solution, shaken for two hours at normal room temperature and, thereafter, passed through a glass filter. The filtrate thus obtained was tested for enzymatic activity. Table 1 shows the relation between various adsorbents used and corresponding amounts of lipid hydrolyzing enzyme adsorbed.

The activity of the lipid hydrolyzing enzyme was measured by the modified Nords' method as follows. The quantity of this enzyme which liberated one microequivalent of acid per minute was taken as the unit for rating the said activity. The measurement was carried out by allowing a reaction solution consisting of 5ml of olive oil emulsion, 4ml of 0.1M phosphate buffer solution (pH 7) and 1 ml of the enzyme under test to undergo reaction for 20 minutes, terminating this reaction by 20ml of a 1:1 mixed solution of acetone-ethanol and titrating the liberated fatty acid with 0.05M NaOH solution. The reaction temperature was 60° C for the measurement of the lipid hydrolyzing enzyme derived from a microorganism of genus *Pseudomonas* and 37° C for the measurement of the enzyme from any other source.

Table 1

| Adsorbent | Amount of lipid hydrolyzing enzyme adsorbed (in units) |
|---|---|
| Laurylamine | 1.62 |
| Stearylamine | 1.58 |
| Oleamide | 0.42 |
| Palmitaimide | 1.40 |
| Ethanolamine | 0.00 |

EXAMPLE 2

By following the procedure of Example 1, 3.4ml of Sepharose 4B was caused to react with 5ml of a mixed solution consisting of ethanol and 0.1M sodium hydrogen carbonate solution containing 0.5M common salt having an aliphatic amine dissolved therein at a concentration of $2 \times 10^{-5}$M/ml. One ml of the resultant product was packed in a column 10.3mm in diameter.

Two ml of the lipid hydrolyzing enzyme (200 units/ml) prepared in the same manner as in Example 1 was applied to the column and washed with Tris buffer. The amount of enzyme consequently eluted was subtracted from the amount of the enzyme added to the column and the found difference, namely the amount of the enzyme adsorbed on the 1 ml of column was taken as the exchange capacity.

Table 2 shows the relation between the numbers of carbon atoms of the aliphatic amines used as the adsorbent and the corresponding values of exchange capacity.

Table 2

| Number of carbon atoms in adsorbent | Exchange capacity (unit) |
|---|---|
| 4 | 0 |
| 6 | 0 |
| 7 | 0 |
| 8 | 52.3 |
| 9 | 16.2 |
| 10 | 106.5 |
| 11 | 80.5 |
| 12 | 112.0 |
| 13 | 79.4 |

Then, the lipid hydrolyzing enzyme adsorbed on the dodecylamine-Sepharose column was washed thoroughly with Tris buffer and the adsorbed lipid hydrolyzing enzyme was eluted by a different kind of eluent. Table 3 shows the relation between the elutents used and the corresponding ratios of elution obtained. In the case of an eluent which affected the activity of the enzyme, the obtained ratio of elution was compensated for the influence of eluate. The surface active agent was used in the form of a solution dissolved in Tris buffer.

Table 3

| Eluent | Ratio of elution (%) |
|---|---|
| 0.1M acetate buffer solution containing 1.5M potassium chloride (pH 4.0) | 0 |
| 0.1M glycin buffer solution containing 1.5M sodium chloride (pH 10.2) | 0 |
| Tris buffer containing 5M guanidine hydrochloride | 2.89 |
| Mixed solution of olive oil emulsion and 0.1M phosphate buffer solution (1 : 1) | 0 |
| Tris buffer containing 0.2M acetic acid and 0.5M sodium chloride | 0 |
| 0.3% sodium deoxycholate | 103.6 |
| 0.5% sodium cholate | 66.3 |
| 0.5% sodium taurocholate | 84.3 |
| 0.5% sodium glycocholate | 88.2 |
| 0.5% sodium oleate | 9.7 |
| 0.5% sodium lauryl sulfate | 101.5 |
| 0.5% Tween 20 | 59.3 |
| 0.5% Tween 80 | 106.1 |
| 0.5% Triton X-100 | 105.9 |
| 0.1% Lipomin COH | 45.0 |

EXAMPLE 3

Figure 1:
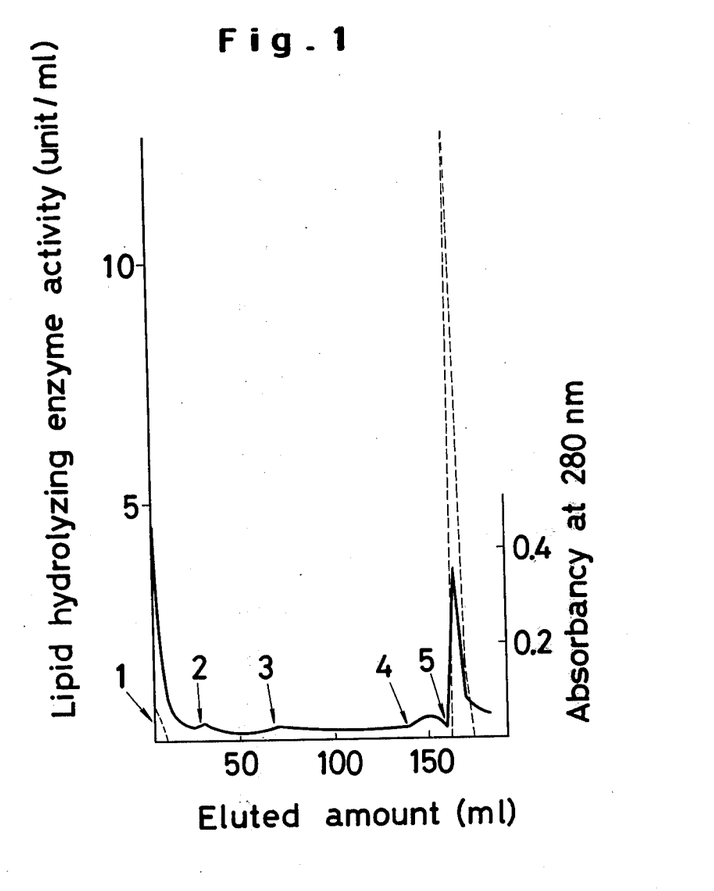
FIG. 1 is an elution curve obtained of a lipid hydrolyzing enzyme produced by a microorganism of genus *Pseudomonas*.
Figure 2:
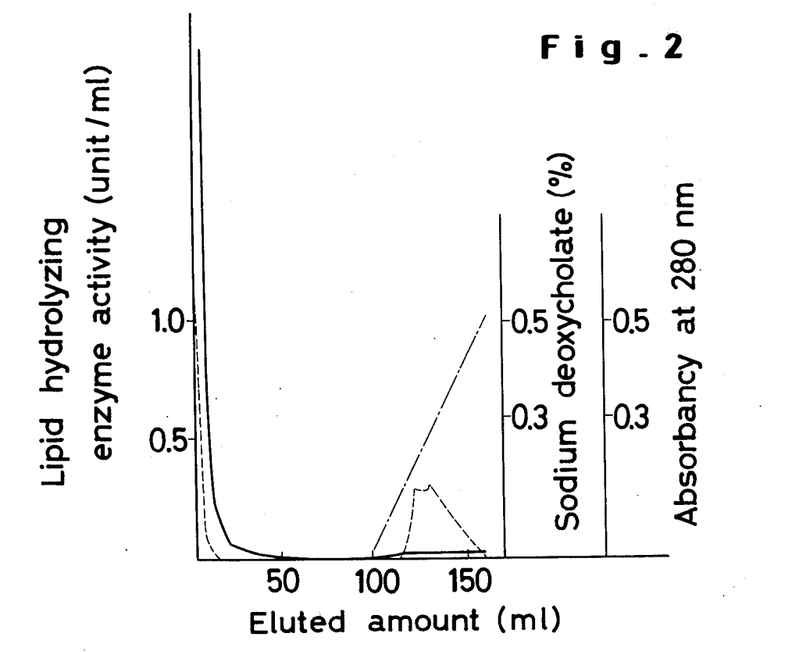
FIG. 2 is an elution curve of a lipid hydrolyzing enzyme from hog.
Figure 3:
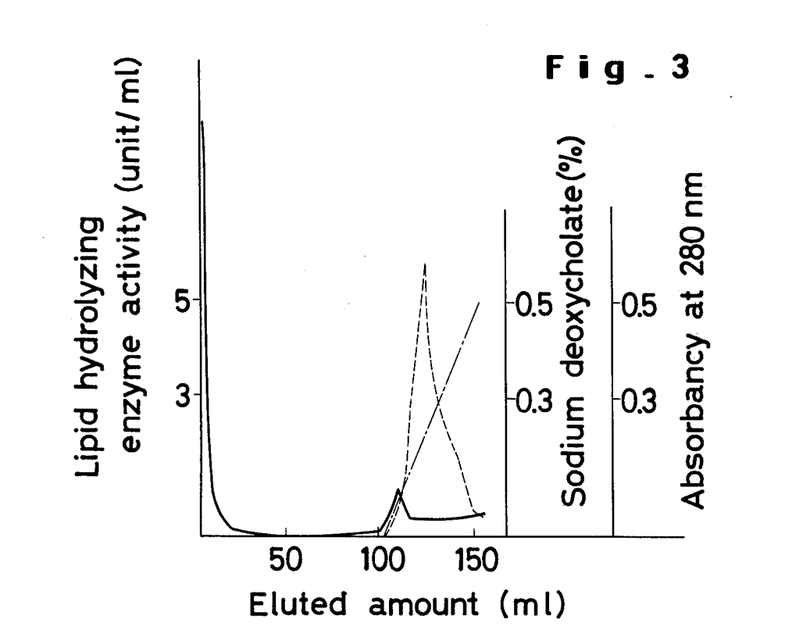
FIG. 3 is an elution curve of a yeast lipase.

Two ml of laurylamine-Sepharose was packed in a column 10.3mm in diameter and equilibrated with Tris buffer. A lipid hydrolyzing enzyme of a different source was dissolved in Tris buffer and 0.2 to 0.5ml of the resultant solution was poured on the column. Then the column was thoroughly washed until there was detected substantially no impurities in the washing. Then, the adsorbed enzyme was eluted with sodium deoxycholate. The elution concentration was in the neighborhood of 0.3%, irrespectively of the source of the lipid hydrolyzing enzyme. Table 4 compares specific activity of the original lipid hydrolyzing enzymes with that of the eluted lipid hydrolyzing enzyme and also shows the recovery ratio of the activity of the enzyme eluted to that of the enzyme added. The specific activity is expressed as the magnitude of the enzyme activity per mg of protein. FIGS. 1 – 3 show the elution curves. The lipid hydrolyzing enzyme from hog pancreas was purchased from Sigma Chemical Co. and the lipid hydrolyzing enzyme from yeast was purchased from Meito Sangyo Co. (N. Tomizika, et al.: Agr. Biol. Chem., 30, 576 (1966)). The lipid hydrolyzing enzyme of a microorganic source was one derived from genus *Pseudomo*- nas (the same as that used in Example 1). The activity measurement was performed at 37° C in the case of the lipid hydrolyzing enzymes from hog pancreas and from yeast. In the case of an enzyme on which a bile salt manifested its effect, the measured value of activity was compensated for the effect.

Table 4

| Source | Degree of refinement | | Recovery ratio (%) |
|---|---|---|---|
| | Specific activity of original solution | Specific activity of eluted solution | |
| Microorganism of genus Pseudomonas | 84.6 | 235.7 | 95.6 |
| Hog pancreas | 1.2 | 53.4 | 57.2 |
| Yeast (Candida cylindracea) | 74.2 | 341.8 | 56.5 |

FIG. 1 shows elution curves obtained of 0.5ml of the lipid hydrolyzing enzyme derived from a microorganism of genus Pseudomonas. The solid line represents the absorbancy at 280 nm of the eluted amount of protein and the dotted line represents the amount of eluted activity. In the graph, 1 and 4 indicate the points at which the elution was made with Tris buffer, 2 indicates the point at which the elution was effected with 0.1M acetate buffer containing 1.5M common salt (pH 5), 3 the point at which the elution was done with a buffer solution (pH 11) consisting of 0.1M sodium hydroxide and 0.1M dibasic sodium phosphate containing 1.5M potassium chloride and 5 the point at which the elution was accomplished with Tris buffer containing 0.5% of sodium deoxycholate.

FIG. 2 shows elution curves obtained of 0.5ml of the lipid hydrolyzing enzyme derived from hog pancreas. In the graph, the alternate one-long and one-short dash line represents the concentration of sodium deoxycholate.

FIG. 3 shows elution curves obtained of 0.2ml of the lipid hydrolyzing enzyme derived from yeast. In the graph, the symbols have the same meaning as those of FIG. 1 and FIG. 2.

EXAMPLE 4

In 5ml of a 1:1 mixed solution consisting of ethanol and 0.1M sodium hydrogen carbonate solution containing 0.5M common salt having $1 \times 10^{-4}$M of an aliphatic amine dissolved therein, 3.4ml of Sepharose 4B activated in advance with cyanogen bromide was dispersed and shaken at normal room temperature for two hours to cause a reaction. The resultant reaction product was filtered by a glass fiber and the filter cake was dispersed in 5ml of 1M ethanolamine solution containing 0.5M common salt (pH 8.0) and shaken at normal room temperature for two hours to cause a reaction, with the result that the preparation of a carrier was completed with the unimpaired active residue kept from the reaction.

Then the produced carrier was washed cyclically with a 1:1 mixed solution consisting of ethanol and 0.1M sodium hydrogen carbonate solution containing 0.5M common salt, 0.1M acetate buffer solution containing 1M common salt (pH 4.0) and a borate buffer solution containing 1M common salt (pH 8.0) in the order mentioned to remove the substance which were bound to the carrier not by covalent bond but by a mere physical adsorbing activity. The washed laurylamine-Sepharose 4B was equilibrated with Tris buffer and put to the subsequent test.

The lipid hydrolyzing enzyme in this case was a crude standard obtained by precipitating at pH 4 the enzyme produced extracellularly by Pseudomonas mephitica var. lipolytica (Bikoken Microorganism Deposit No. 520), extracting the precipitate at pH 8 and dialyzing the extracted precipitate against water for one week.

The activity per ml of the lipid hydrolyzing enzyme was 80 units and the specific activity or the magnitude of activity per mg of protein was 43.7.

One ml of laurylamine-Sepharose 4B prepared as described above was packed in a column 10.3mm in diameter and 2ml of the lipid hydrolyzing enzyme solution (specific activity 43.7) was added to the column. The column was washed with 16ml of Tris buffer. Thereafter, the adsorbed lipid hydrolyzing enzyme (130 units) was eluted with a mixed solution consisting of acetone and 0.1M sodium hydrogen carbonate solution containing 0.5M common salt. The recovery ratio of the lipid hydrolyzing enzyme was 101.5% and the specific activity was 163.

The measurement of the activity was carried out by the same method as in Example 1.

EXAMPLE 5

Undecylamine-Sepharose 4B was prepared by following the procedure of Example 4. One ml of this undecylamine-Sepharose 4B was packed in a column 10.3mm in diameter and 2ml of the lipid hydrolyzing enzyme was applied thereto. The column was washed with 13ml of Tris buffer and the adsorbed lipid hydrolyzing enzyme (106.4 units) was eluted with a mixed solution consisting of Tris buffer and ethanol. The recovery ratio of the lipid hydrolyzing enzyme was 62.9% and the specific activity increased to 2.04 times the original level.

EXAMPLE 6

In 5ml of a 1:1 mixed solution consisting of ethanol and 0.1M sodium hydrogen carbonate solution containing 0.5M common salt having $1 \times 10^{-4}$M of a different adsorbent of Table 5 dissolved therein, there was dispersed 3.4ml of Sepharose 4B activated in advance with cyanogen bromide. The resultant dispersion was shaken at normal room temperature for two hours to effect a reaction. The resultant reaction mixture was passed through a glass filter. The filter cake was dispersed in 5ml of 1M ethanolamine solution containing 0.5M common salt (pH 8.0) and shaken at normal room temperature for two hours, with the result that the preparation of a carrier accomplished with the unimpaired reactive residue protected from the reaction.

Then, the carrier was washed cyclically with a 1:1 mixed solution consisting of ethanol and 0.1M sodium hydrogen carbonate solution containing 0.5M common salt, 0.1M acetate buffer solution containing 1M common salt (pH 4.0) and a borate buffer solution containing 1M common salt (pH 8.0) in the order mentioned to remove substances which were bound to the carrier not by covalent bond but by a mere physical adsorbing activity. The washed insoluble carrier was equilibrated with Tris buffer and put to the subsequent test.

The lipid hydrolyzing enzyme used in this case was a crude standard obtained by precipitating at pH 4 the lipid hydrolyzing enzyme produced extracellularly by *Pseudomonas mephitica* var. *lipolytica* (Bikoken Microorganism Deposit No. 520), extracting the precipitate at pH 8 and dialyzing the extracted precipitate against water for one week. The activity of the enzyme per ml was 80 units and the specific activity or the magnitude of activity per mg of protein was 43.7.

One ml of Sepharose 4B having an aromatic derivative bound thereto was packed in a column 10.3mm in diameter and 2ml of the lipid hydrolyzing enzyme was applied thereto. The column was washed with 16ml of Tris buffer. The amount of the enzyme consequently eluted was subtracted from the amount of the enzyme added to the column and the found difference, namely the amount of the enzyme adsorbed on the 1ml of column was taken as the exchange capacity. The measurement of the enzymatic activity was carried out by the same method as in Example 1.

Table 5 shows the relation between the aromatic derivatives used as adsorbents and the corresponding values of exchange capacity.

Table 5

| Kind of adsorbent | Exchange capacity (unit/ml of Sepharose derivative) |
| --- | --- |
| Phenylpropylamine | 110.8 |
| Phenylethylamine | 119.3 |
| Phenylmethylamine | 113.6 |

In the case of phenylmethylamine-Sepharose 4B, elution of the lipid hydrolyzing enzyme was still observed after washing had been given with 16ml of Tris buffer. In the case of phenylpropylamine or phenylethylamine, however, once the washing was given with 6ml of Tris buffer, substantially no elution of activity was observed even when additional Tris buffer was passed. The results indicated that two or more carbon chains would give a sufficient length to the spacer which served the purpose of connecting Sepharose 4B with the benzene ring.

When the lipid hydrolyzing enzyme adsorbed on phenylpropylamine-Sepharose 4B was eluted with 0.5% sodium lauryl sulfate, the recovery ratio of the enzyme was 73.8% and the specific activity at the maximum increased to 4.98 times. The measurement of the activity was performed after the eluted solution had been diluted to ten times the original volume so as to eliminate the otherwise possible effect of sodium lauryl sulfate.

EXAMPLE 7

A Sepharose possessed of hexanoic acid as the spacer was synthesized by binding 6-aminohexanoic acid to Sepharose 4B activated in advance with cyanogen bromide. This product was named as CH-Sepharose. One (1) millimol of a different adsorbent shown in Table 6 was placed in 50% dioxane solution and, with the pH value adjusted in the range of from 4.5 to 6.0, 4ml of CH-Sepharose was suspended therein. A solution having 400mg of 1-ethyl-3-(3-dimethylaminopropyl) carbodiimide hydrochloride dissolved in 2ml of distilled water was added to the suspension. The resultant mixture was shaken at normal room temperature for 24 hours, with the pH value thereof managed to be kept in the range of from 4.5 to 6.0, to synthesize an insoluble carrier having a hydrophobic residue attached thereto. The synthesized insoluble carrier was washed with 50% dioxane and an acid and an alkali in the same way as in Example 1 and finally equilibrated with Tris buffer before it was put to the subsequent test.

Similarly to Example 6, 1ml of Sepharose 4B derivative having a different adsorbent attached thereto was packed in a column and 2ml of the lipid hydrolyzing enzyme (specific activity 43.7) was applied thereto. Then the column was washed with 16ml of Tris buffer to find exchange capacity. Subsequently, the lipid hydrolyzing enzyme adsorbed on the insoluble carrier was eluted with Tris buffer containing 0.5% of sodium deoxycholate. Table 6 shows the exchange capacity for each adsorbent used, the recovery ratio of the enzyme eluted with sodium deoxycholate and the highest value of specific activity found in all the 3-ml fractions obtained.

Table 6

| Adsorbent | Exchange capacity (unit/ml Sepharose) | Recovery ratio (%) | Specific activity (unit/mg of protein) |
| --- | --- | --- | --- |
| CH-Sepharose alone | 12.31 | 0.29 | — |
| 6-Aminochrysene | 124.93 | 97.9 | 86.3 |
| Cyclohexylamine | 125.09 | 102.7 | 401.1 |
| 2-Aminopyridine | 133.06 | 71.5 | 107.1 |

The lipid hydrolyzing enzyme adsorbed on the insoluble carrier having attached thereto 2-aminopyridine as the adsorbent was eluted with 3M guanidine hydrochloride. In this case, the recovery ratio of the enzyme was 64.6% and the specific activity was 54.16. The activity of the lipid hydrolyzing enzyme was measured of what was obtained by causing the solution eluted with the 3M guanidine hydrochloride to be immediately put into a cool room to be dialyzed overnight against Tris buffer.

EXAMPLE 8

A Sepharose possessed of hexylamine as the spacer was synthesized by binding 1,6-diaminohexane to Sepharose 4B activated in advance with cyanogen bromide and it was named as AH-Sepharose. One millimol of deoxycholic acid was placed in 50% of dioxane solution and the solution was adjusted to a pH value in the range of from 4.6 to 6.0. In this solution was suspended 4ml of AH-Sepharose. A solution having 400mg of 1-ethyl-3-(3-dimethylaminopropyl) carbodiimide hydrochloride dissolved in 2ml of distilled water was added to the suspension. The resultant mixture, with the pH value managed to be adjusted in the range of from 4.5 to 6.0, was shaken at normal room temperature for 24 hours to produce a synthetic insoluble carrier having attached thereto deoxycholic acid. The synthesized insoluble carrier was washed with 50% dioxane, an acid and an alkali in the same manner as in Example 1.

One ml of Sepharose 4B derivative having the aforementioned deoxycholic acid attached thereto was packed, as in Example 1, in a column and 2ml of the lipid hydrolyzing enzyme (specific activity 43.7) was applied thereto. The carrier was then washed with 16ml of Tris buffer. The exchange capacity was found to be 137.4 units/ml of Sepharose 4B derivative. When the carrier was subsequently washed with 0.02M phosphate buffer solution (pH 6) containing 1M of common salt, no elution of the enzyme was detected. Then Tris buffer containing 1M of common salt and 0.1M $Na_2H$-$PO_4$-HaOH buffer solution (pH 11) containing 1.5M potassium chloride were passed through the column but no elution of the enzyme could be detected. When Tris buffer containing 0.5% of sodium deoxycholate was finally passed through the column, a lipid hydrolyzing enzyme having a specific activity of 157.9 was obtained at a recovery ratio of 100.35%.

To the AH-Sepharose, the lipid hydrolyzing enzyme tested was ionically adsorbed. The greater part of this adsorbed lipid hydrolyzing enzyme was eluted with Tris buffer containing 1M of common salt.

EXAMPLE 9

An insoluble carrier having attached thereto a different aromatic amine as the adsorbent was packed in a column in the same way as in Example 1 and 2ml of a lipid hydrolyzing enzyme was applied thereto. Then the carrier was washed with 16ml of Tris buffer and thereafter washed with a different organic solvent to elute the adsorbed enzyme. Table 7 shows the various organic solvents used and the corresponding values of activity recovery ratio obtained by elution.

Table 7

| Organic solvent | Adsorbent | Activity recovery ratio |
| --- | --- | --- |
| Mixed solution (1:1) of water and dioxane | Phenylmethyl-amine | 38.0(%) |
| Mixed solution (1:1) of water and ethylene glycol | Phenylethyl-amine | 2.53(%) |
| Mixed solution (1:1) of sodium solution of acetone | | 70.4(%) |

An insoluble carrier having attached thereto cyclohexylamine as the adsorbent was packed in a column in the same manner as in Example 1, 2ml of a lipid hydrolyzing enzyme solution (specific activity 43.7) was applied thereto. The carrier was washed with 16ml of Tris buffer and the adsorbed lipid hydrolyzing enzyme (125.1 units) was eluted with a mixed solution consisting of ethanol and 0.1M sodium hydrogen carbonate solution containing 0.5M of common salt. The recovery ratio of the enzyme was 95.9% and the specific activity was 90.8.

We claim:

1. A method for separating a lipid hydrolyzing enzyme whose molecules have outwardly exposed hydrophobic residues from a solution containing said enzyme, which comprises:
   1. bringing said crude lipid hydrolyzing enzyme solution into contact with an insoluble carrier having a hydrophobic organic compound directly or through a spacer attached thereto forming a hydrophobic residue for thereby causing the lipid hydrolyzing enzyme contained in said crude lipid hydrolyzing enzyme solution to be adsorbed by the hydrophobic residue onto said insoluble carrier, said hydrophobic residue being a hydrophobic residue of the organic compound, the organic compound being an aromatic, alicyclic or heterocyclic compound, and
   2. exposing the lipid hydrolyzing enzyme adsorbed on said hydrophobic residue to contact with one member selected from the group consisting of a liquid containing a surface active agent, a liquid containing a protein denaturing agent and an organic solvent miscible with water for thereby eluting the lipid hydrolyzing enzyme into the liquid.

2. The method of claim 1 wherein said hydrophobic residue of said organic compound is selected from the group consisting of the benzene, chrysene, cyclohexane, deoxycholic acid and pyridine groups.

3. The method of claim 1, wherein the hydrophobic organic compound is a primary amine.

4. The method of claim 3, wherein the amine contains as a hydrophobic residue, an aromatic hydrocarbon residue, or an alicyclic hydrocarbon residue.

5. The method of claim 1, wherein the hydrophobic residue is cyclohexane.

6. The method of claim 1, wherein the hydrophobic residue is pyridine.

7. The method of claim 1, wherein the hydrophobic residue is chrysene.

8. The method of claim 1, wherein the hydrophobic organic compound is deoxycholic acid.

9. The method of claim 1, wherein the surface active agent is one member selected from the group consisting of bile salt, sodium oleate, sodium lauryl sulfate, polyoxyethylene sorbitan monolaurate, polyoxyethylene sorbitan monoleate, p-t-octylphenoxypolyethoxyethanols and 1-hydroxyethyl-1-carboxysodium-2-alkyl-2-imidazolinium hydroxide.

10. The method of claim 1, wherein the protein denaturing agent is one member selected from the group consisting of guanidine hydrochloride and urea.

11. The method of claim 1, wherein the organic solvent miscible with water is one member selected from the group consisting of ethanol, methanol, acetone, dioxane and ethylene glycol.

* * * * *